(12) United States Patent
Hansen et al.

(10) Patent No.: US 11,090,346 B2
(45) Date of Patent: Aug. 17, 2021

(54) CANNABINOID COMPOSITION AND METHOD OF SUBLINGUAL, BUCCAL AND ORAL MUCOSA DELIVERY

(71) Applicant: InBold Inc., Santa Cruz, CA (US)

(72) Inventors: Kenda Hansen, Aptos, CA (US); Kathleen Grave, Aptos, CA (US)

(73) Assignee: InBold Inc., Santa Cruz, CA (US)

( * ) Notice: Subject to any disclaimer, the term of this patent is extended or adjusted under 35 U.S.C. 154(b) by 0 days.

(21) Appl. No.: 16/424,351

(22) Filed: May 28, 2019

(65) Prior Publication Data

US 2020/0376057 A1 Dec. 3, 2020

(51) Int. Cl.

| | |
|---|---|
| *A61K 36/185* | (2006.01) |
| *A61K 47/36* | (2006.01) |
| *A61K 31/714* | (2006.01) |
| *A61K 38/48* | (2006.01) |
| *A61K 47/46* | (2006.01) |
| *A61K 47/26* | (2006.01) |
| *A61K 47/12* | (2006.01) |
| *A61K 31/05* | (2006.01) |
| *A61K 9/00* | (2006.01) |
| *A61K 31/192* | (2006.01) |
| *A61K 31/352* | (2006.01) |
| *A61K 47/38* | (2006.01) |

(52) U.S. Cl.
CPC .......... *A61K 36/185* (2013.01); *A61K 9/006* (2013.01); *A61K 31/05* (2013.01); *A61K 31/192* (2013.01); *A61K 31/352* (2013.01); *A61K 31/714* (2013.01); *A61K 38/4873* (2013.01); *A61K 47/12* (2013.01); *A61K 47/26* (2013.01); *A61K 47/36* (2013.01); *A61K 47/38* (2013.01); *A61K 47/46* (2013.01); *C12Y 304/22004* (2013.01)

(58) Field of Classification Search
None
See application file for complete search history.

(56) References Cited

U.S. PATENT DOCUMENTS

| | | | |
|---|---|---|---|
| 5,064,654 A | 11/1991 | Berner | |
| 5,254,346 A | 10/1993 | Tucker | |
| 5,716,928 A | 2/1998 | Benet | |
| 6,113,940 A | 9/2000 | Brooke | |
| 6,328,992 B1 | 12/2001 | Brooke | |
| 8,435,556 B2 | 5/2013 | Stinchcomb | |
| 9,011,825 B2 * | 4/2015 | Midha | A61K 8/84 424/52 |
| 9,029,423 B2 | 5/2015 | Whittle | |
| 9,044,390 B1 * | 6/2015 | Speier | A61K 36/00 |
| 9,561,251 B2 * | 2/2017 | Weibel | A61K 9/2095 |
| 9,827,282 B2 | 11/2017 | Naheed | |
| 9,827,322 B2 | 11/2017 | Naheed | |
| 10,143,755 B2 | 12/2018 | Borja | |
| 10,188,628 B1 | 1/2019 | Kershman | |
| 10,206,888 B2 | 2/2019 | Vu | |
| 2007/0293580 A1 * | 12/2007 | Hill | A61K 31/137 514/649 |
| 2017/0368020 A1 * | 12/2017 | Estey | A61K 9/0058 |

OTHER PUBLICATIONS https://en.wikipedia.org/wiki/Siraitia_grosvenorii—accessed May 12, 2020.*
Hidese, S. et al (Oct. 2019). "Effects of L-Theanine Administration on Stress-Related Symptoms and Cognitive Functions in Healthy Adults: A Randomized Controlled Trial," Nutrients 11(10):2362, 13 pages.
Ranade, M. et al. (Jan. 2017). "A Simple Dietary Addition Of Fenugreek Seed Leads To The Reduction In Blood Glucose Levels: A Parallel Group, Randomized Single-Blind Trial," Ayu 38(1-2): 24, 1-5.
Rathnavelu, V. et al. (Sep. 2016). "Potential Role Of Bromelain In Clinical And Therapeutic Applications," Biomedical Reports 5(3):283-288.
Shannon, S. et al. (2019, e-pub Jan. 7, 2019). "Cannabidiol In Anxiety And Sleep: A Large Case Series," The Permanente Journal 23:5 pages.
Stough, C. et al. (2014). "Reducing Occupational Stress With A B-Vitamin Focussed Intervention: A Randomized Clinical Trial: Study Protocol," Nutrition Journal 13(1):122, 12 pages.
U.S. Appl. No. 16/402,128, filed May 2, 2019, for Kenda Hansen et al. A copy of the U.S. Patent Application is not submitted herewith pursuant to the waiver of 37 C.F.R. § 1.98(a)(2)(iii) issued by the Office on Sep. 21, 2004.

* cited by examiner

*Primary Examiner* — Susan Hoffman
(74) *Attorney, Agent, or Firm* — Morrison & Foerster LLP

(57) ABSTRACT

A formulation includes a cannabinoid extract that is pharmaceutically effective by systemic delivery via a recipient's oral mucosal lining. The method of delivery avoids the digestive tract processing and liver metabolizing of the active ingredients of the formulation, whereby lower doses cause a desired therapeutic effect or other intended effect. Variations of the formulation include a cannabinoid extract and one or more of pregelatinized tapioca starch polymethylsilsesquioxane, bromelain, volume Fenugreek gum, vitamin B12, luo han guo fruit extract, mannitol, microcrystalline cellulose, sodium alginate, gellan gum, menthol Natural peppermint flavor or oil, Grapefruit flavored powder or oil, magnesium stearate and/or citric acid. The cannabinoid extract may include Tetrahydrocannabinol, tetrahydrocannabinolic acid, Cannabidiol, Cannabidiol acid, and/or other cannabinoid sourced from a *Cannabis sativa* plant. The formulation includes at least one cannabinoid in a volume and measure that is pharmaceutically effective and/or effectual in achieving an intended systemic state or response of the recipient.

18 Claims, 3 Drawing Sheets

Figure 1:
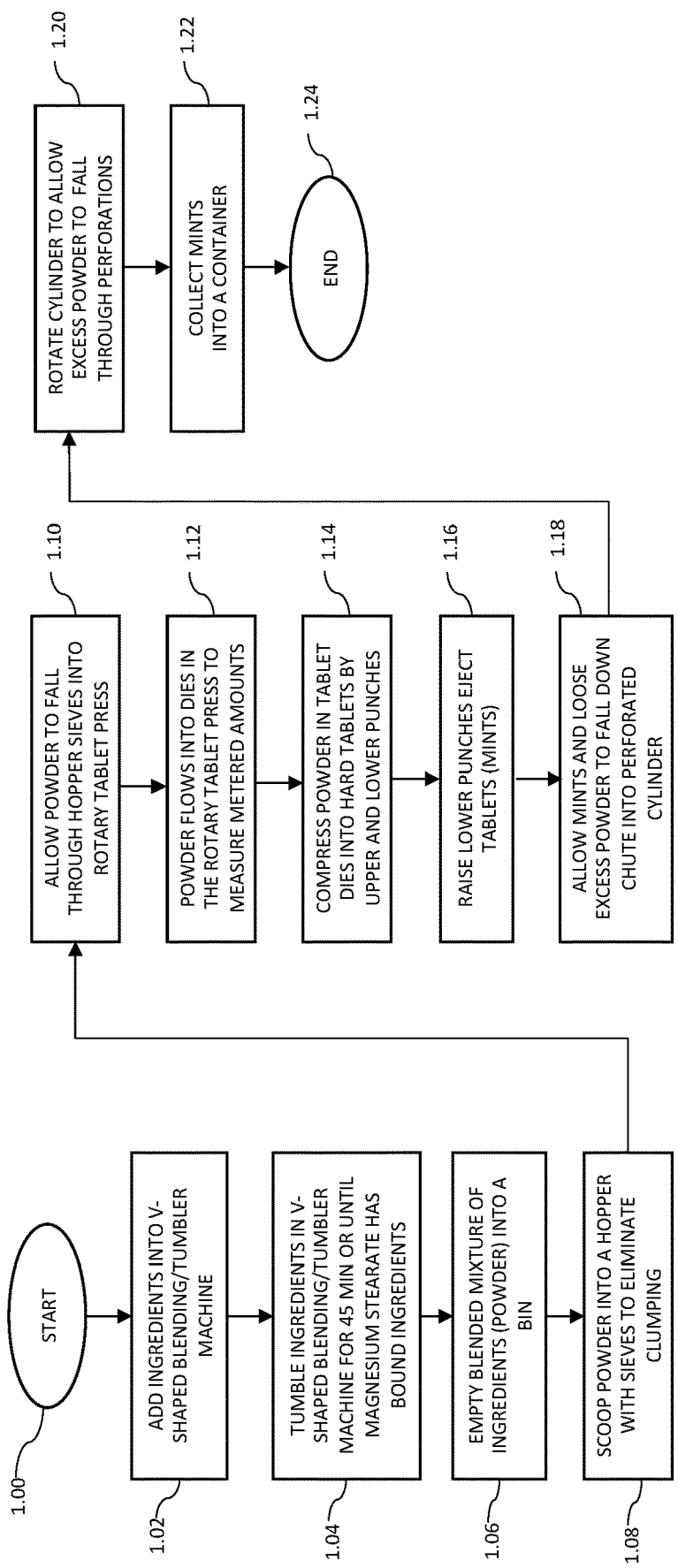

| Ingredient List (INCI) | mg | mg range | Function |
|---|---|---|---|
| Cannabinoids, CBD and other variations | 5 | 5 - 20 | Key ingredient |
| Mannitol | 10 | 10 - 50 | Sweetness |
| Microcrystalline cellulose | 8 | 3 - 15 | |
| Sodium Alginate | 5 | 0.0 - 8.0 | |
| Gellan Gum | 2 | 0 - 5 | |
| Fenugreek gum | 2 | 0.0 - 5.0 | Vegan, and alternative to guar gum |
| B12 | 1 | .5 - 3.0 | liposomal delivery & reduce inflammation |
| Natural peppermint flavor (optional) | 1 | 0 - 2.0 | natural menthol OR similar peppermint |
| Grapfruit flavored powder (optional) | 0 | 0 - 1 | |
| Bromelain | 0.05 | .05 - 3.0 | Inflammation and absorption |
| Luo Han Guo fruit extract (Monk Fruit) | 1 | 0.25 - 2.0 | diabetic alternative & very sweet need less |
| Magnesium Stearate | 0.25 | 0.25 - 1.0 | |
| Pregelatinized Tapioca starch polymethylsilsesquioxane | 0.75 | 0.25 - 2.0 | Or 0.10% to 6.00% of the weight of the total weight the unit dose |
| Citric acid | 1.95 | 0.0- 2.0 | |
| Total | 50 | 50 - 75 | |

FIGURE 2

| 300 | 302 ADDITIONAL INGREDIENT NAME | 304 LOW END MEASURE | 306 PREFERRED MEASURE |
|---|---|---|---|
| 308A | ADDITIONAL INGREDIENT NAME | LOW END MEASURE | PREFERRED MEASURE |
| 308B | Vitamin A | 1000 mcg | 7,000 mcg |
| 308C | Vitamin D | 5 mcg | 100 mcg |
| 308D | Vitamin C | 5 mg | 75 mg |
| 308E | Magnesium ( enzyme ) | 10 mg | 75 mg |
| 308F | Gaba (amino acid) | 20 mg | 75 mg |
| 308G | 5-hydroxytryptophan ( amino acid) | 20 mg | 100 mg |
| 308H | Passionflower ( Passiflora) oil | 20 mg | 100 mg |
| 308I | Lavender (essential oil) | 0.015 mg | 1 mg |
| 308J | Licorice | 20 mg | 100 mg |
| 308K | liposomes | Zero or 0.25 mg | 5 mg |
| 308L | peanut butter powder | 5 mg | 100 mg |
| 308M | liver powder | 5 mg | 100 mg |
| 308N | Acacia gum (fiber, binder) | Zero or 25 mg | 5 mg |
| 308O | Sunflower lecithin powder | Zero 0.5 mg | 5mg |
| 308P | Silica Dioxide (Absorbs liquid turning liquid ingredients into free-flowing powders that can be implemented into formula.) | Zero or 0.25 mg | 5 mg |
| 308Q | Dicalcium Phosphate (Ensures tablets can be shaped and solidified with ease.) | Zero or 0.25 mg | 5 mg |
| 308R | Lemon Balm | Zero to 2 mg | 2 mg |

FIGURE 3

CANNABINOID COMPOSITION AND METHOD OF SUBLINGUAL, BUCCAL AND ORAL MUCOSA DELIVERY

FIELD OF THE INVENTION

This disclosure relates generally to compositions that include at least one cannabinoid, and particularly to formulated cannabinoid mixtures that enable sublingual delivery of a volume of at least one cannabinoid.

BACKGROUND OF THE INVENTION

The terms sublingual and buccal are defined herein to refer to avenues of medication administration achieved via the mouth of a human or other mammal. Sublingual drug delivery involves placing the instant drug under a recipient's tongue to dissolve and be absorbed in the recipient's tissue. Buccal drug delivery requires placing a drug between an oral gum and cheek of a recipient, whereby the instant drug dissolves and is absorbed into the circulatory system of the recipient.

The cheek and locations under the tongue of many mammals typically present numerous, pharmaceutically accessible capillaries of a potential recipient's circulatory system. Medications and other biologically active materials can thus by-pass the mammalian digestive system and be absorbed directly into a drug recipient's circulatory system.

Sublingual and buccal drug delivery are most advantageous when rapid introduction into the recipient's system is desired, when the recipient's stomach is expected to be resistive to absorbing the instant drug, and/or digesting the instant drug is likely to decrease the benefits of the instant drug. More particularly, avoiding the metabolizing imposed by the liver can lower the required effective dose for some potential drug recipients. Additionally, and particularly in the case of many animals pets, livestock, and domesticated mammals, drug delivery methods that eliminate the need for swallowing or injections is often highly desirable.

Various cannabinoids have medically beneficial effects. Medical marijuana is helpful to people who experience chronic non-cancer pain, vomiting and nausea caused by chemotherapy. Formulations containing Tetrahydrocannabinol (hereinafter, "THC"), the principal psychoactive constituent sourced from the *Cannabis sativa* plant, can help with treating symptoms of AIDS patients. Furthermore, animal studies show cannabinoids found in marijuana may have analgesic and anti-inflammatory effects, antitumor effects, and anticancer effects, including the treatment of breast and lung cancer.

Medical *Cannabis* (or medical marijuana) refers to the use of *Cannabis* and its constituent cannabinoids, such as Cannabidiol (hereinafter "CBD"), as medical therapy to treat disease or alleviate symptoms. *Cannabis* has been used to reduce nausea and vomiting in chemotherapy and people with AIDS, and to treat pain and muscle spasticity.

Medical *Cannabis* can be administered by a variety of routes in the prior art, including vaporizing or smoking dried bud and leaf portions, eating leaf or extracts, and taking capsules.

An aromatic terpenoid, THC has a very low solubility in water, but good solubility in most organic solvents, specifically lipids and alcohols. In general, THC has mild to moderate analgesic effects, and *Cannabis* can be used to treat pain by altering transmitter release on dorsal root ganglion of the spinal cord and in the periaqueductal gray. Other effects include relaxation, alteration of visual, auditory, and olfactory senses, fatigue, and appetite stimulation. THC has marked antiemetic properties, and may also reduce aggression in certain subjects. Evidence suggests that THC helps alleviate symptoms suffered both by AIDS patients, and by cancer patients undergoing chemotherapy, by increasing appetite and decreasing nausea. It has also been shown to assist some glaucoma patients by reducing pressure within the eye, and is used in the form of *Cannabis* by a number of multiple sclerosis patients, who use it to alleviate neuropathic pain and spasticity.

CBD is one of at least 85 cannabinoids found in *Cannabis*. It is a major constituent of the *Cannabis sativa* plant, second to THC, and represents up to 40% in its extracts. Compared with THC, CBD is not psychoactive in healthy individuals, and is considered to have a wider scope of medical applications than THC, including to epilepsy, multiple sclerosis spasms, anxiety disorders, bipolar disorder, schizophrenia, nausea, convulsion and inflammation, as well as inhibiting cancer cell growth.

*Cannabis* growers have been developing different strains of *Cannabis* plants that have different THC and CBD levels. Medical *Cannabis* users have been demanding medical *Cannabis* products that have CBD as the main active ingredient, and little or no THC, providing some of the medicinal benefits of *Cannabis* without the psychoactive effects caused mainly by THC.

The prior art fails to optimally address the full range of modalities of sublingual delivery of cannabinoids for either medical treatment or recreational use. It is therefore a long-felt need to provide novel and effective formulations for the sublingual or buccal delivery of one or more cannabinoids to a human recipient, many types of domestic pest and certain domesticated or wild mammals.

SUMMARY OF THE INVENTION

Towards this object and other objects that are made obvious to one of ordinary skill in the art in light of the present disclosure, the present invention (hereinafter, "the invented formulation") may be or be comprised within any of a number of variations of the invented formulation that include a cannabinoid extract and are effective for systemic delivery via a recipient's oral mucosal lining. One or more alternate preferred embodiments of the invented formulation may include an extract of a cannabinoid containing plant material, wherein the extract may contain one or more cannabinoid active agents, or a combination of the extract and one or more additional cannabinoid active agents, in a volume and measure that are pharmaceutically effective. Certain alternate preferred embodiments of the invented formulation may include one or more active cannabinoids selected from the group consisting of (a) partially or completely purified cannabinoid compounds, (b) synthetic cannabinoid compounds, and (c) mixtures thereof.

Certain still alternate preferred embodiments of the invented formulation may optionally, additionally or alternatively comprise a volume of pregelatinized tapioca starch polymethylsilsesquioxane, a volume of bromelain and/or a volume of Fenugreek gum. Certain other alternate preferred embodiments of the invented formulation my optionally, additionally or alternatively comprise vitamin B12, luo han guo fruit extract, mannitol, microcrystalline cellulose, sodium alginate, gellan gum, menthol *Mentha piperita* oil, *Citrus grandis* peel oil, magnesium stearate and/or citric acid. One or more alternate preferred embodiment of the invented formulation that contain the pregelatinized tapioca starch polymethylsilsesquioxane preferably include the pregelatinized tapioca starch polymethylsilsesquioxane in the range of from 0.10% to 6.00% by weight based on the weight of a unit dose of the entire comprising formulation.

Even other alternate preferred embodiments of the invented formulation may optionally, additionally or alternatively comprise a portion or volume of lemon balm, licorice or licorice extract, natural or synthesized peppermint flavoring, natural or synthesized grapefruit flavoring powder, *Passiflora* oil and/or extract, and/or Lavender oil and/or extract.

In various alternate preferred embodiments of the invented formulation, an extract of the cannabinoid containing plant material is present in the comprising formulation in the range of from 6% to 20% by weight based on the entire comprising formulation.

In additional alternate preferred embodiments of the invented formulation, the invented formulation includes a cannabinoid first active agent and one or more additional cannabinoid active agents are independently selected from the group consisting of a measure or volume of THC, tetrahydrocannabinolic acid (hereinafter, "THC Acid"), CBD, cannabidiolic acid (hereinafter, "CBD Acid"), cannabigerolic acid, cannabigerol, cannabigerovarinic acid, cannabigerolovarin, cannabichromenic acid, cannabichromene, cannabidivarin, cannabidivarinic acid, tetrahydrocannabivarinic acid, tetrahydrocannabivarin, cannabivarinic acid, cannabivarin, cannabinolic acid, cannabinol, and isomers thereof, and mixtures thereof. The CBD and/or the CBD Acid may be present among the top five most predominantly present cannabinoid materials in still additional alternate preferred embodiments of the invented formulation.

Yet additional alternate preferred embodiments of the invented formulation includes a cannabinoid first active agent and one or more additional materials such as Vitamin A, Vitamin D, Vitamin C, Magnesium enzyme, Amino acid Gaba, Amino acid 5-hydroxytryptophan, liposomes, peanut butter powder, liver powder, Acacia gum, Sunflower lecithin powder, Silica Dioxide, and/or Dicalcium Phosphate.

The method of the present invention (hereinafter, "the invented method") includes an administration of a cannabinoid material comprising a preferred embodiment of the invented formulation by a placement of the instant invented formulation within a recipient's mouth and proximate to the recipient's oral mucosal lining. A portion of the recipient's oral mucosal lining selected for placement of a preferred embodiment of the invented formulation may be sublingual or approximate to the recipient's oral gum and an interior side of a facial cheek.

This Summary is provided to introduce a selection of concepts in a simplified form that are further described below in the Detailed Description. This Summary is not intended to identify key features or essential features of the claimed subject matter, nor is it intended to be used to limit the scope of the claimed subject matter.

INCORPORATION BY REFERENCE

All publications, patents, and patent applications mentioned in this specification are herein incorporated by reference to the same extent as if each individual publication, patent, or patent application was specifically and individually indicated to be incorporated by reference. U.S. Pat. No. 10,285,971 titled "Formulations of water-soluble derivatives of vitamin E and soft gel compositions, concentrates and powders containing same" issued on May 14, 2019 to Inventor Bromley; U.S. Pat. No. 10,272,125 titled "Transdermal delivery of cannabidiol with other active moieties including cannabinoids" issued on Apr. 30, 2019 to Inventor Weimann; U.S. Patent 20020136752 titled "PHARMACEUTICAL FORMULATIONS" issued on Sep. 26, 2002 to Inventors Whittle et al.; U.S. Pat. No. 10,258,601 titled "Vaporizable cannabinoid compositions" issued on Apr. 16, 2019 to Inventors Perry et al.; U.S. Pat. No. 10,238,577 titled "Oral delivery device and methods" issued on Mar. 26, 2019 to Inventors Gjertsen et al.; U.S. Pat. No. 10,137,161 titled "Medical *Cannabis* lozenges and compositions thereof" issued on Nov. 27, 2018 to Inventors Kolsky et al.; U.S. Pat. No. 10,064,821 titled "Low-temperature inhalation administration of cannabinoid entities" issued on Sep. 4, 2018 to Inventors Eck et al.; U.S. Pat. No. 10,028,919 titled "Lipid nanoparticle compositions and methods as carriers of cannabinoids in standardized precision-metered dosage forms" issued on Jul. 24, 2018 to Inventors Kaufman et al.; U.S. Pat. No. 9,730,911 titled "*Cannabis* extracts and methods of preparing and using same" issued on Aug. 15, 2017 to Inventors Verzura et al.; U.S. Pat. No. 9,717,683 titled "Low-temperature inhalation administration of cannabinoid entities" issued on Aug. 1, 2017 to Inventors Eck et al.; U.S. Pat. No. 9,695,143 titled "Prodrugs of tetrahydrocannabinol, compositions comprising prodrugs of tetrahydrocannabinol and methods of using the same" issued on Jul. 4, 2017 to Inventor Stinchcomb et al.; U.S. Pat. No. 9,504,723 titled "Medical *Cannabis* lozenges and compositions thereof" issued on Nov. 29, 2016 to Inventors Kolsky et al.; U.S. Pat. No. 9,308,175 titled "Dosage unit for sublingual, buccal or oral administration of water-insoluble pharmaceutically active substances" issued on Apr. 12, 2016 to Inventors Pellikaan et al.; U.S. Pat. No. 8,980,942 titled "Prodrugs of tetrahydrocannabinol, compositions comprising prodrugs of tetrahydrocannabinol and methods of using the same" issued on Mar. 17, 2015 to Inventor Stinchcomb et al.; U.S. Pat. No. 8,906,429 titled "Medical *Cannabis* lozenges and compositions thereof" issued on Dec. 9, 2014 to Inventors Kolsky et al. are incorporated herein by reference in their entirety and for all purposes.

BRIEF DESCRIPTIONS OF THE DRAWINGS

The invention will now be further and more particularly described, by way of example only, and with reference to the accompanying drawings in which:

FIG. 1 is a process chart of fabricating various alternate preferred embodiments of the invented formulations in accordance with the invented method; c FIG. 2 is a formulary chart presenting various essential and optional ingredients and compositional ranges thereof of various alternate preferred embodiments of the invented formulation that may be generated in accordance with the method of FIG. 1; and FIG. 3 an additional formulary chart presenting various additional optional ingredients and compositional ranges thereof of various alternate preferred embodiments of the invented formulation of the invented formulation that may be generated in accordance with the method of FIG. 1.

DETAILED DESCRIPTION

Referring now generally to the Figures and particularly to FIG. 1, FIG. 1 is a process chart of fabricating various alternate preferred embodiments of the invented formulations in accordance with the invented method.

In a first step 1.00 of the method of FIG. 1, a process of formulating a present mixture is initiated. In step 1.02, the compounder selectively adds one or more of the ingredients disclosed herein into a V-shaped blending or tumbler machine, to include adding two or more substances listed in FIG. 2 or FIG. 3 or otherwise disclosed in the present Application.

In step 1.04 the compounder utilizes the V-shaped blending or tumbler machine of step 1.02 to tumble the ingredients for a duration of 45 minutes or until the ingredient magnesium stearate has bound the ingredients. In step 1.06 the compounder empties the blended mixture of ingredients (hereinafter the "powder") out of the blender and into a bin. In step 1.08 the compounder scoops the powder into a hopper with sieves to eliminate clumping in the powder. In step 1.10, the holes in the sieves of the hopper allow the powder to fall through, and empty into a rotary tablet press. In step 1.12, the powder flows into dies in the rotary tablet press and is thus measured into metered amounts. In step 1.14 the compounder compresses the powder in the dies into hard tablets by means of upper punches and lower punches of the rotary tablet press. In step 1.16 the compounder raises the lower punches and ejects the compressed powder tablets (hereinafter, the "mints") from the dies of the rotary tablet press. In step 1.18 the compounder allows the mints and any loose excess powder to fall down a chute and into a perforated cylinder. In step 1.20 the compounder rotates the perforated cylinder to allow the loose excess powder to fall away through the perforations. Finally, in step 1.22 the finished mints are collected into a container and the process of FIG. 1 ends at step 1.24.

Referring now generally to the Figures and particularly to FIG. 2, FIG. 2 is an ingestible formulary table 200 of unit dose formulation listings and presenting both an exemplary unit dose formulation of alternate preferred embodiments of the invented formulation. Various possible, alternative and optional ingredients of alternate preferred embodiments of the invented formulation are listed in a first column 202. Exemplary ingredient measures are listed in a second column 204 and are associated by inclusion in a same row with individual alternative and optional ingredients. Ranges of ingredient magnitudes of said alternative and optional ingredients thereof presented in a third column 206 and are associated by inclusion in a same row with individual alternative and optional ingredients. Brief descriptions of a function and potential benefits derived from including the listed ingredients may be displayed in a fourth column 208.

A header row 210A labels the first column 202, the second column 204, the third column 206, and the fourth column 208 for easy legibility of the table 200.

A row 210B indicates that, for the ingredient Cannabinoids, CBD and other variations, an exemplary unit dose is 5.0 milligrams, the unit dose range is 5.0 milligrams-20 milligrams, and its function is as the key ingredient.

A row 210C indicates that, for the ingredient Mannitol, an exemplary unit dose is 10 milligrams, the unit dose range is zero to 50 milligrams, and its function is to provide sweetness.

A row 210D indicates that, for the ingredient Microcrystalline cellulose, an exemplary unit dose is 8 milligrams, and the unit dose range is 3.0 milligrams-15.0 milligrams.

A row 210E indicates that, for the ingredient Sodium Alginate, an exemplary unit dose is 5 milligrams, and the unit dose range is zero to 8.0 milligrams.

A row 210F indicates that, for the ingredient Gellan Gum, an exemplary unit dose is 2 milligrams, and the unit dose range is 0 milligrams-5 milligrams.

A row 210G indicates that, for the ingredient Fenugreek gum, an exemplary unit dose is 2 milligrams, the unit dose range is from zero to 5.0 milligrams, and its function is as an alternative to guar gum that may optionally be accepted as a vegan identified substance.

A row 210H indicates that, for the ingredient B12, an exemplary unit dose is 1 milligram, the unit dose range is zero to 3.0 milligrams, and its function is as a liposomal delivery system and inflammation reducer.

A row 210I indicates that, for the ingredient Menthol/ *Mentha piperita* (Peppermint) oil, an exemplary unit dose is 1 milligram, the unit dose range is 0 milligrams-2.0 milligrams, and its function is as natural menthol or smaller peppermint.

A row 210J indicates that, for the ingredient *Citrus grandis* (Grapefruit) peel oil, an exemplary unit dose is 0 milligrams, and the unit dose range is 0 milligrams-1.0 milligram.

A row 210K indicates that, for the ingredient Bromelain, an exemplary unit dose is 0.05 milligrams, the unit dose range is 0.05 milligram-3.0 milligrams, and its function is reducing inflammation and improving absorption.

A row 210L indicates that, for the ingredient Luo Han Guo fruit (Monk Fruit) extract, an exemplary unit dose is 1 milligram, the unit dose range is 0.25 milligram-2.0 milligrams, and its function is as a strong sweetener that's also safe for diabetics.

A row 210M indicates that, for the ingredient Magnesium Stearate, an exemplary unit dose is 0.25 milligram, and the unit dose range is 0.25 milligram-1.0 milligram.

A row 210N indicates that, for the ingredient Pregelatinized Tapioca starch polymethylsilsesquioxane, an exemplary unit dose is 0.75 milligram, the unit dose range is 0.25 milligram-2.0 milligrams, and its function is as v. talc.

A row 210O indicates that, for the ingredient Citric acid, an exemplary unit dose is 1.95 milligram, and the unit dose range is from zero to 2.0 milligrams.

A row 210P lists that the total volume of the listed ingredients in an exemplary ingestible unit dose combined may be 50 milliliters, and the total volume of the combined ingredients will range from 50 milligrams to 75 milligrams.

Referring now generally to the Figures and particularly to FIG. 3, FIG. 3 is an ingestible formulary table 300 of alternate and optional ingredients of various alternate preferred embodiments of the invented formulation. Various possible, alternative and optional ingredients of alternate preferred embodiments of the invented formulation are listed in a first column 302. Exemplary low end ingredient measures of a unit dose of the invented formulation of the named ingredients are presented in a second column 304 and are associated by inclusion in a same row with individual alternative and optional ingredients. Exemplary magnitudes of measures of a unit dose of the invented formulation of the named ingredients are presented in a third column 306 and are associated by inclusion in a same row with individual alternative and optional ingredients.

A header row 308A labels the first column 302, the second column 304, and the third column 306 for easy legibility of the additional ingredient table 300.

A row 308B indicates that the optional ingredient Vitamin A may be combined in the step 1.02 in the range that includes a low measure of 1,000 microGram (hereinafter. "mcg") and a preferred measure of 7,000 mcg.

A row 308C indicates that the optional ingredient Vitamin D may be combined in the step 1.02 in the range that includes a low measure of 5.0 mcg and a preferred measure of 100 mcg.

A row 308D indicates that the optional ingredient Vitamin C may be combined in the step 1.02 in the range that includes a low measure of 5.0 mcg and a preferred measure of 75 mcg.

A row 308E indicates that the optional ingredient Magnesium enzyme may be combined in the step 1.02 in the range that includes a low measure of 10.0 mcg and a preferred measure of 75 mcg.

A row 308F indicates that the optional ingredient Gaba amino acid may be combined in the step 1.02 in the range that includes a low measure of 20.0 milliGrams (hereinafter, "mg") and a preferred measure of 75 mg.

A row 308G indicates that the optional ingredient 5-hydroxytryptophan amino acid may be combined in the step 1.02 in the range that includes a low measure of 20.0 mg and a preferred measure of 100 mg.

A row 308H indicates that the optional ingredient Passionflower/*Passiflora* oil may be combined in the step 1.02 in the range that includes a low measure of 20.0 mg and a preferred measure of 100 mg.

A row 308I indicates that the optional ingredient Lavender oil may be combined in the step 1.02 in the range that includes a low measure of 1.015 mg and a preferred measure of 1.0 mg.

A row 308J indicates that the optional ingredient licorice extract may be combined in the step 1.02 in the range that includes a low measure of 20 mg and a preferred measure of 100 mg.

A row 308K indicates that the optional ingredient of a volume of liposomes may be combined in the step 1.02 in the range that includes a low measure of none to 0.25 mg and a preferred measure of 5.0 mg.

A row 308L indicates that the optional ingredient of a volume of peanut butter powder or oil may be combined in the step 1.02 in the range that includes a low measure of 0.5 mg and a preferred measure of 100 mg.

A row 308M indicates that the optional ingredient of a volume of liver powder or liver element may be combined in the step 1.02 in the range that includes a low measure of 5.0 mg and a preferred measure of 100 mg.

A row 308N indicates that the optional ingredient of a volume of acacia gum may be combined in the step 1.02 in the range that includes a low measure of zero to 0.25 mg and a preferred measure of 5 mg. It is understood that the volume of acacia gum may optionally be included in certain various alternate preferred embodiments of the invented formulation to provide fiber and act as a binder of various alternate preferred embodiments of the invented formulation the process of FIG. 1.

A row 308O indicates that the optional ingredient of a volume of Sunflower lecithin powder may be combined in the step 1.02 in the range that includes a low measure of zero to 0.5 mg and a preferred measure of 5 mg.

A row 308P indicates that the optional ingredient of a volume of Silica. Dioxide may be combined in the step 1.02 in the range that includes a low measure of zero to 0.25 mg and a preferred measure of 5 mg. It is understood that Silica Dioxide may optionally be included in certain various alternate preferred embodiments of the invented formulation to absorb liquid and thereby turn other liquid ingredients of the invented formulation into free-flowing powders that can be better combined in the process of FIG. 1.

A row 308Q indicates that the optional ingredient of a volume of Dicalcium Phosphate may be combined in the step 1.02 in the range that includes a low measure of zero to 0.25 mg and a preferred measure of 5 mg. It is understood that Dicalcium Phosphate may optionally be included in certain various alternate preferred embodiments of the invented formulation to better ensure that tablets fabricated by the method of FIG. 1 might be shaped and solidified with ease.

A row 308R indicates that the optional ingredient of a volume of lemon balm may be combined in the step 1.02 preferably within the range of from zero to 2.0 milligrams.

The terms "formulation", "mixture", "combination", and "blend" are each defined herein to have a range of meaning that includes a substance made of two or more different materials, such as solutions, emulsifications, stirred materials, mixed materials, combinations, chemically-reacted or -reacting materials, compounded materials, adhering materials, and/or other suitable substances comprising chemical substances located within a gel, ointment, cataplasm, poultice, paste, cream, lotion, plaster, or jelly. The terms "mixing" "combining" and "blending" are each defined herein to have a range of meaning that includes a process of one or more steps that joins or co-locates two or more differing materials to form one or more suitable substances type known in the art, such as solutions, emulsifications, blends, stirred materials, mixed materials, combinations, chemically-reacted or -reacting materials, compounded materials, adhering materials, and/or other suitable substances comprising chemical substances located or positioned within a gel, ointment, cataplasm, poultice, paste, cream, lotion, plaster, or jelly.

In understanding the scope of the present invention, the term "comprising" and its derivatives, as used herein, are intended to be open ended terms that specify the presence of the stated features, elements, components, groups, integers, and/or steps, but do not exclude the presence of other unstated features, elements, components, groups, integers and/or steps. The foregoing also applies to words having similar meanings such as the terms, "including", "having" and their derivatives. Also, the terms "part", "section", "portion", "member", or "element" when used in the singular can have the dual meaning of a single part or a plurality of parts. Finally, terms of degree such as "substantially", "about", and "approximately" as used herein mean a reasonable amount of deviation of the modified term such that the end result is not significantly changed.

While selected embodiments have been chosen to illustrate the invented system, it will be apparent to those skilled in the art from this disclosure that various changes and modifications can be made herein without departing from the scope of the invention as defined in the appended claims. For example, the size, shape, location, or orientation of the various components can be changed as needed and/or desired. Components that are shown directly connected or contacting each other can have intermediate structures disposed between them. The functions of one element can be performed by two, and vice versa. The structures and functions of one embodiment can be adopted in another embodiment, it is not necessary for all advantages to be present in a particular embodiment at the same time. Every feature which is unique from the prior art, alone or in combination with other features, also should be considered a separate description of further inventions by the applicant, including the structural and/or functional concepts embodied by such feature(s). Thus, the foregoing descriptions of the embodiments according to the present invention are provided for illustration only, and not for the purpose of limiting the invention as defined by the appended claims and their equivalents.

We claim:

1. A sublingual formulation comprising:
   a) an extract of a cannabinoid containing *Cannabis* plant material, said extract containing one or more first cannabinoid active agent(s) or a combination of said extract and one or more additional cannabinoid active agent(s), said additional cannabinoid active agent(s) selected from the group consisting of partially or completely purified cannabinoid compounds, synthetic cannabinoid compounds, and mixtures thereof;
   b) a pregelatinized tapioca starch;
   c) volume of bromelain;
   and d) a volume of gamma-aminobutyric acid (GABA).

2. The formulation of claim 1 further comprising fenugreek gum.

3. The formulation of claim 1 further comprising vitamin B12.

4. The formulation of claim 1 further comprising luo han guo fruit extract.

5. The formulation of claim 1 further comprising mannitol.

6. The formulation of claim 1 further comprising microcrystalline cellulose.

7. The formulation of claim 1 further comprising sodium alginate.

8. The formulation of claim 1 further comprising gellan gum.

9. The formulation of claim 1 further comprising menthol or *Mentha piperita* oil.

10. The formulation of claim 1 further comprising *Citrus grandis* peel oil or lemon balm.

11. The formulation of claim 1 further comprising magnesium stearate.

12. The formulation of claim 1 further comprising citric acid.

13. The formulation of claim 1, wherein the extract of the cannabinoid containing *Cannabis* plant material is in the range of from 6% to 20% by weight based on the entire formulation.

14. The formulation of claim 1, wherein the pregelatinized tapioca starch is present in the range of from 0.10% to 6% by weight based on the entire formulation.

15. The formulation of claim 14, wherein the extract of the cannabinoid containing *Cannabis* plant material is present in the range of from 6% to 20% by weight based on the entire formulation.

16. The formulation of claim 1 wherein the cannabinoid first active agent(s) and the additional cannabinoid active agent(s) are independently selected from the group consisting of a tetrahydrocannabinol (THC), a tetrahydrocannabinolic acid (THC Acid), cannabidiol (CBD), cannabidiolic acid (CBD Acid), cannabigerolic acid, cannabigerol, cannabigerovarinic acid, cannabigerolovarin, cannabichromenic acid, cannabichromene, cannabidivarin, cannabidivarinic acid, tetrahydrocannabivarinic acid, tetrahydrocannabivarin, cannabivarinic acid, cannabivarin, cannabinolic acid, cannabinol, and isomers thereof, and mixtures thereof.

17. The formulation of claim 16 wherein said CBD and said CBD Acid are present among the top five most predominantly present cannabinoid materials in said formulation.

18. A method of administration of a cannabinoid material comprising administering the formulation of claim 1 to a subject via a sublingual placement of the formulation.

* * * * *